United States Patent [19]
Hughes et al.

[11] Patent Number: 5,149,184
[45] Date of Patent: Sep. 22, 1992

[54] WORK STATION WITH PHOTOTHERAPY LIGHT BOX

[76] Inventors: Philip Hughes, 34 Yacht Club Dr., Lake Hopatcong, N.J. 07849; Michael Terman, 14 E. 4th St., New York, N.Y. 10012

[21] Appl. No.: 472,424

[22] Filed: Jan. 19, 1990

Related U.S. Application Data

[63] Continuation of Ser. No. 175,953, Mar. 31, 1988, abandoned.

[51] Int. Cl.⁵ .......................... F21V 21/06; A61N 1/00
[52] U.S. Cl. .................................. 362/1; 362/33; 362/220; 362/230; 362/260; 362/287; 128/395; 128/396
[58] Field of Search ................. 362/1, 2, 33, 217, 220, 362/221, 230, 260, 287, 154, 394, 156; 128/395, 396

[56] References Cited

U.S. PATENT DOCUMENTS

| | | | |
|---|---|---|---|
| 4,091,441 | 5/1978 | Ott | 362/1 |
| 4,120,025 | 10/1978 | Deaven | 362/154 |
| 4,254,449 | 3/1981 | Benasutti et al. | 362/33 |
| 4,287,554 | 9/1981 | Wolft | 362/225 |
| 4,335,724 | 6/1982 | Frei et al. | 128/396 |
| 4,404,619 | 9/1983 | Ferguson | 362/225 |
| 4,740,707 | 4/1988 | Thaw | 128/396 |

FOREIGN PATENT DOCUMENTS 3023752  1/1982  Fed. Rep. of Germany ...... 128/396

*Primary Examiner*—Ira S. Lazarus
*Attorney, Agent, or Firm*—Darby & Darby

[57] ABSTRACT

A combined work station and phototherapy unit in which the fixture containing the light source is mounted on a vertical support to be placed on the base of the open area for work to be performed, the fixture being at an angle, preferably in the range of 30°-60°, so that the user will not be staring directly into the light from the fixture. There will be light both impringing upon the eyes of the user for photobiological effect and also light will be directed to the work area.

18 Claims, 2 Drawing Sheets

WORK STATION WITH PHOTOTHERAPY LIGHT BOX

This is a continuation of application Ser. No. 175,953, filed Mar. 31, 1988 now abandoned.

BACKGROUND OF THE INVENTION

The present invention relates to a phototherapy unit (light source) used as a work station. Various publications in the art have shown that the human subjected to light of the proper illumination intensity and the correct dosages can be provided with a number of advantageous results. For example, it can be used to treat seasonal affective disorder (SAD), reduce fatigue, adjust sleep onset and awakening, etc.

Prior art phototherapy devices, a bank of light sources are generally provided. The light sources are mounted in a stationary horizontally standing lighting fixture and the user stands or sits in front of, or slightly to one side, of the fixture or an illuminated table surface. The user looks toward the light source or indirectly receives the light therefrom by looking to the side. Such fixtures require that the person sit three feet from light for two or more hours in early morning/evening. Most active people find the lengthy sessions difficult to maintain or comply with. If higher levels of illumination are used, e.g., 5,000 to 10,000 lux, to shorten exposure duration by sitting closer or using higher output light sources in the fixture, then the brightness and visual discomfort are excessive. In addition, such devices were not designed to permit the patient to engage in ambulatory activities while he or she is receiving the hours of light therapy treatment. Such treatment will become widely acceptable only if session duration can be sufficiently reduced, which is achievable for the first time with minimal visual discomfort with the present invention.

BRIEF DESCRIPTION OF THE INVENTION

The subject invention is directed to a combined phototherapy unit and work station. The work station serves as a support for the light fixture which contains a number of light sources, such as fluorescent lamps, which are to provide the therapeutic modality by light. It also provides a space within which the subject can perform a normal task, such as for example, reading, writing, computer work, eating breakfast, or any other close in type of work. The fixture is mounted on the work station so that when the person is working, the light is in a superior position, that is, primarily above the person's line of sight. This positions the person much closer to the light providing higher light levels for shorter treatment sessions without visual discomfort. The user is therefore able to perform normal work or recreation tasks while receiving the correct amount of light for shorter phototherapy treatment sessions due to the position of the fixture relative to the person. In addition, the unit includes the capability to control the amount of light output that the fixture produces at the person's face thus allowing for individual differences in dose, i.e., duration of exposure times illumination level.

OBJECTS OF THE INVENTION

It is therefore an object of the present invention to provide a combined work station and phototherapy unit.

Another object of the invention is to provide a work station which serves as a support for a phototherapy unit in which the phototherapy unit is mounted in the work station at a superior position to the user so that the light does not intrude directly into the line of sight of the user when performing visual tasks.

An additional object is to provide a phototherapy unit for use in a work station which permits the subject to perform normal work or recreation functions while receiving controlled doses of light for therapeutic and/or nontherapeutic energizing purposes. The ability to control an individual's dose, i.e., duration time intensity, is important, for individuals vary in required dose; therefore flexibility and control of dose is an object of this invention.

Yet another object is to provide a combined work station and phototherapy unit in which the phototherapy fixture is detachable from and separately usable apart from the work station. When used upon awakening under the preferred therapeutic schedule for counteracting seasonal affect disorder, i.e., winter depression, or delayed sleep phase, the unit may be placed, or used, in the bedroom and switched on automatically by a 24-hour timer as a potent adjunct to substitute for an alarm clock which itself may fail to elicit arousal or awakening.

A further object is to provide a therapeutic level of light intensity within a confined area, permitting installation in multiuser office or industrial spaces, or for optimal use in lounges during work breaks, in a spacial arrangement that will not be distractive to people nearby who are working or resting under normal room illumination.

BRIEF DESCRIPTION OF THE DRAWINGS

Other objects and advantages of the present invention will become more apparent upon reference to the following specification and annexed drawings in which.

DETAILED DESCRIPTION OF THE INVENTION

Figure 1:
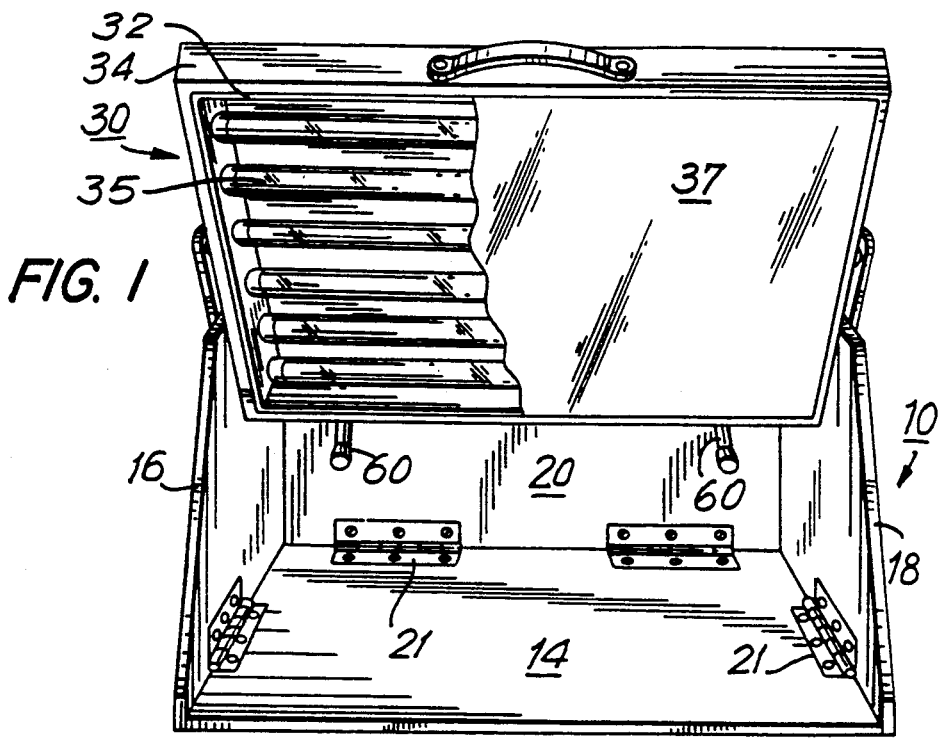
FIG. 1 is a perspective view showing the combined work station phototherapy unit in extended form.

FIG. 1 shows the combined work station phototherapy unit 10 in an unfolded form. It includes a bottom base 14 from which are connected by hinges 21 to side walls 16 and 18 and a back wall 20. The side walls 16, 18 are hingedly mounted to the base 14 so that they can fold inwardly with respect to the base. The back wall 20 is hingedly mounted to the base 14 so as to fold under the base. Yet another version of work station excludes the lower back wall 20 using instead a center connecting strip between the side walls 16, 18. The various components 14, 16, 18 and 20 of the work station can be made of any suitable material, e.g., wood, composition board, plastic, etc., or reflective fabric may be used for floor and sides to produce a hemisphere in which an adjustable stand can be placed.

To assemble the work station, the back wall 20 is unfolded from the base 14 and placed in a vertical position and the two side walls 16 and 18 are also unfolded and extended vertically. The side walls 16 and 18 are locked to the back wall 20 by any suitable arrangement, such as, for example, a hook and an eye, spring type latches on the back wall and extending prongs on the side walls (or vice versa), etc. The former type of fasteners are preferred so that the unit can be easily packed for transportability. Alternatively, the fastening can be accomplished by more permanent means such as adhesives, screws, etc. In any event, when the work station 10 is assembled as shown in FIG. 1, it provides a stable platform.

The light source phototherapy fixture 30 has a generally rectangular frame 34 which, for decorative purposes, matches the decor of the base unit 10. Mounted in the frame 34 is a fixture housing 32, preferably of metal, which holds a plurality of light sources. The interior of the lamp fixture housing 32 preferably is made non-gloss white which gives high reflectance and low glare. In the preferred embodiment, there are six fluorescent lamps 35. The fixture 12 contains the usual electrical ballasts (not shown) for providing current to the fluorescent lamps, the sockets for mounting each end of the fluorescent lamps, with wiring between the ballasts and a power cord for connecting the ballast to a source of current.

In addition, total light output is increased approximately forty percent by use of a highly efficient interior reflector surface, e.g., 3-M silver lux coating.

In the preferred embodiment of the invention, there are six fluorescent lamps of either 2, 3 or 4 feet length, although any suitable length can be used. The lamps are preferably of the Vita-Lite type sold by Duro-Test Corporation of North Bergen, N.J. Vita-Lite is a full spectrum fluorescent lamp which has a high coloring index, i.e., it produces light which closely matches that of the natural daylight spectrum, including that in the ultraviolet range. The fixture 32 also can have a diffuser panel 37 in front of the bank of lamps. The diffuser is primarily to more evenly spread out the light and preferably passes most of the light spectrum produced by the lamps. If desired however, the diffuser can be used to block out selected wavelengths, for example, the ultraviolet wavelengths. Alternatively, special daylight simulating fluorescent lamps with a special coating that blocks ultraviolet transmission can be used in the fixture, e.g., Duro-Test Color Guard lamps, or lumen output can be maximized by the use of tri-phosphor lamps, e.g., General Electric SPX lamps.

In a preferred embodiment there is also a switching arrangement for the lamps so that pairs of lamps can be switched on and off. That is, the unit can be operated with either two, four or six lamps on at the same time. Such switches are conventional. In this manner, the output of illumination of the system can be controlled. At the low setting, i.e., two lamps, the illumination level provided is approximately 3300 lux, sufficient to produce phototherapeutic effects at the longer two hour durations. At the high setting, six lamps, the illumination level is approximately 10,000 lux, sufficient to produce phototherapeutic effects in thirty minutes.

Figure 2:
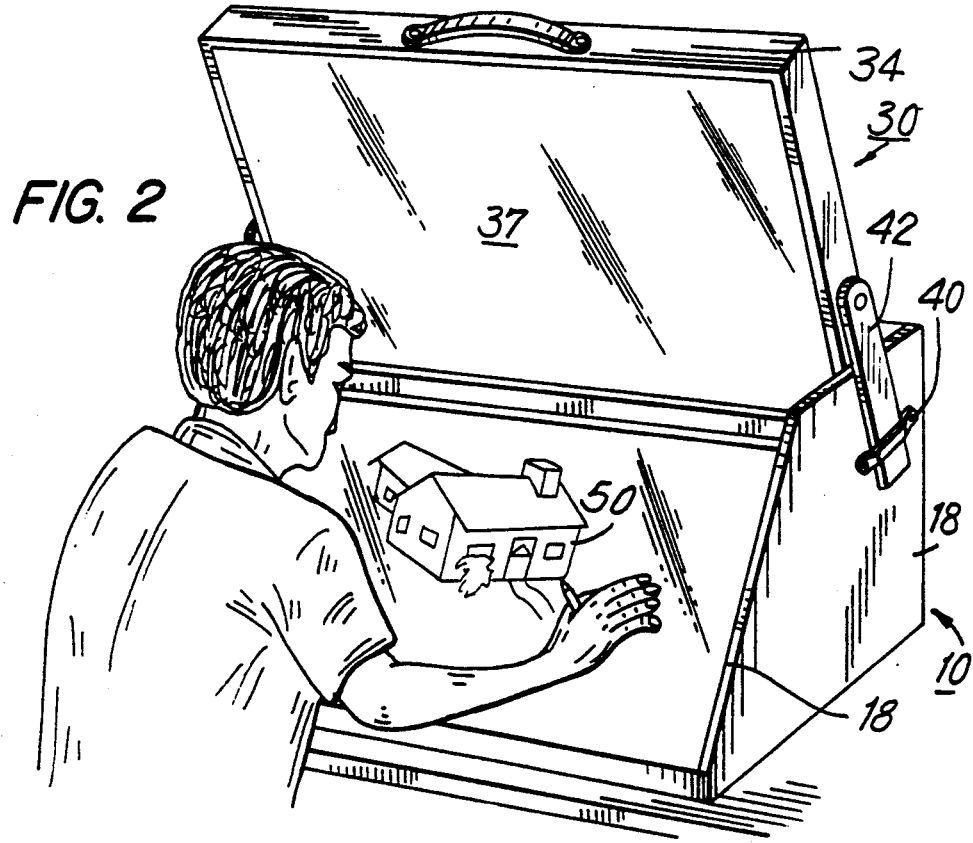
FIG. 2 is a perspective view showing a user positioned in front of the unit.

As seen in FIG. 2, a mounting channel 40 of generally U-shape is mounted to the outside of each of the side walls 16 and 18 (only one is shown in FIG. 2). An arm 42 extends from each side of the fixture frame 32. The fixture frame 34 fits in the space between the two side walls 16 and 18 as shown in FIG. 1 and each arm 42 extends into the respective mounting channel 40 on the side wall. In this manner, the fixture frame and fixture are attached to the work station.

As seen, the fixture frame 34 is mounted at an angle relative to the horizontal. This can be, in a preferred embodiment of the invention, somewhere between 30°-60° and preferably about 40°-45°. If desired the mounting arrangement for the frame arms 42 can be made adjustable relative to the horizontal from 0°-90° so that the fixture, mounting angle can be chosen by the user. When at 0° horizontal the fixture stands upright and can be used for general room illumination.

FIG. 2 schematically shows a user positioned in front of the work station. The workpiece 50, e.g., reading, writing, any physical unit to be assembled or modified, is located on the work station base 14. Light from the fixture 32 radiates into the work space to illuminate the workpiece. The base is preferably set on a table of standard height, e.g., 30 inches and the user sits on a chair. Alternately, the unit may be used at 27 inch height to accommodate a computer or typewriter keyboard. As seen, a normal sized user will be situated relative to the lamp fixture 32 so that when he is looking into the work space in the interior of the work station 10, he will not be looking directly into the light coming out from the lamp fixture 32. That is, as the user looks into the work space, the light from the angularly mounted fixture does not come directly into the user's eyes from a fully frontal direction. In essence, the work station properly positions the user in front of the angularly mounted fixture and the user receives the correct amount of dosage of light while working. Normally, such close positioning of the user to such a large bank of lamps is uncomfortable, preventing the use of the high levels of illumination, i.e., 10,000 lux, found effective for short duration phototherapy, i.e., less than forty-five minute sessions. In the subject invention, the highest intensity levels come from the most superior position above the horizontal line of sight with a gradual decrease in intensity directly down to the line of sight. The positioning of the lamps with most of the light above the line of sight simulates overhead sky conditions with decreasing brightness below the horizontal line of sight. Also, below the line of sight, there is minimal brightness. This greatly decreases user discomfort and, in fact, users consider the light exposure pleasing and invigorating to work under.

By switching off pairs of lamps, with the user in a relatively close position to the work station, and the lamps being three feet in length, approximately 10,000, 6,600 and 3,300 lux illumination intensity levels can be provided by switching from six to four to two, 30 watt 3 foot fluorescent lamps.

As shown in FIG. 1, support legs 60 can be provided on the lower end of the fixture frame 34 so that the fixture can be provided and removed from the work station 10 and permitted to stand on its own.

Figure 3:
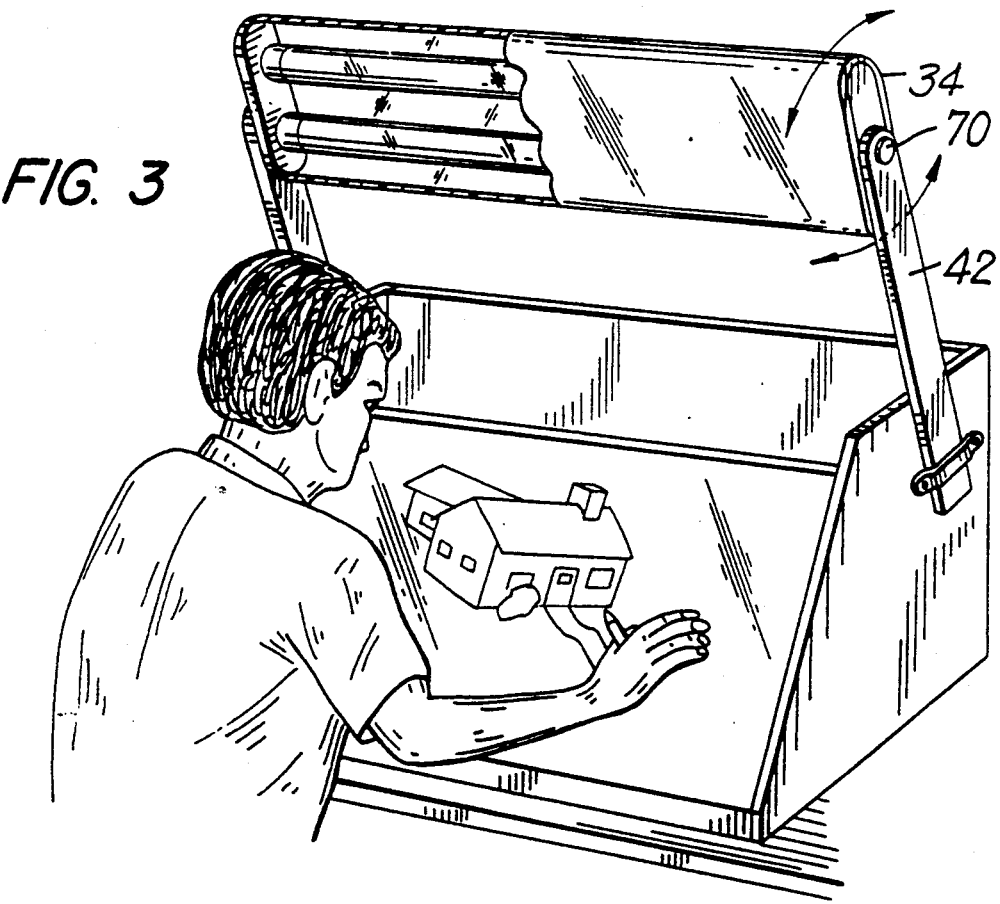
FIG. 3 and 4 are perspective views of further embodiments which use a rotatable support for the fixture.
Figure 4:
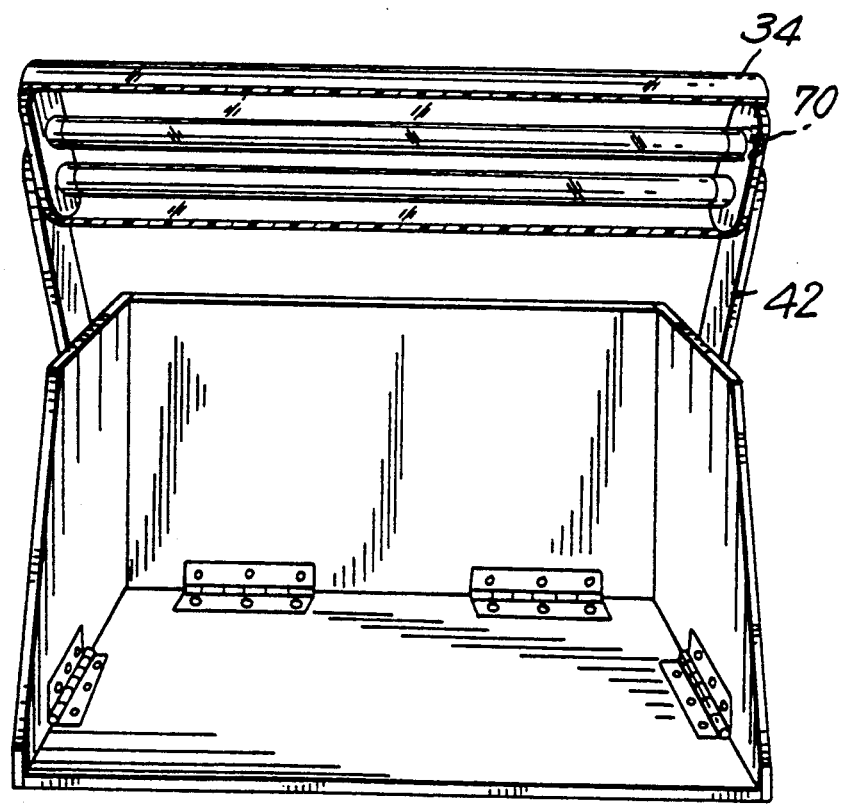

In another embodiment of this invention as seen in FIG. 3 and 4 the phototherapy unit can be of smaller dimensions for compactness, i.e., 2' by 2', 1' by 3', etc., by the use of brackets and arms that extend in from the work station to hold the unit in a superior position in front of the user. FIG. 3 shows such an embodiment for a 10"×3, unit which can contain two or three 30 watt fluorescent lamps. High light levels can be maintained because light unit is optimally positioned above the person's face in the most superior position above the horizontal line of sight. A rotating pivot joint 70 where the light fixture frame 34 attaches to the support arm 42 allows for rotation of the fixture frame 34 clockwise and counter-clockwise so that light can be directed upward, downward, frontward or backward for general and/or indirect room illumination when not being used in the therapeutic mode.

The invention provides a combined work station and light unit which allows the subject to receive high enough light levels to shorten exposure treatment duration to less than forty-five minutes without objectionable visual discomfort to viewer. Furthermore, the illumination level provided achieves that recommended for fine, critical visual performance by the guidelines of the Illuminating Engineering Society of North America, but rarely available in home, office or industrial work areas. It also provides a wide range of selectable illumination levels, thru switching of the component light sources, allowing the user and/or clinician to determine individually the most effective combination of exposure intensity and duration that achieves an optimum therapeutic and/or energizing response. Furthermore, by switching exposure level downward after a therapy session, the system can be used to provide a visually enriched long term working area, without risk of over-exposure to recommended therapeutic doses.

What is claimed is:

1. A combined work station and phototherapy unit for use by a person comprising:
   a portable base unit having vertically extending support means to rest on a surface and define an interior work space which is to be illuminated,
   a light fixture associated with said base unit having at least one electric lamp therein for producing a visible light output, and
   means for mounting said light fixture to said base unit to be located above said work space and to place said electric lamp at an angle in the range of between about 30° to about 60° relative to the horizontal and at a height to supply the visible light output produced by the lamp to a person working at the place where the work station is located both in line and at least in part from a superior position relative to the line of sight of the person.

2. The combined work station and phototherapy unit of claim 1 wherein said vertically extending supports are walls which define a generally rectangular work space area.

3. The combined work station and phototherapy unit of claim 2 wherein said base unit includes a base member, and back and side walls hingedly connected to said base member.

4. The combined work station and phototherapy unit of claim 1 wherein said electric lamp of said fixture comprises a bank of fluorescent lamps.

5. The combined work station and phototherapy unit of claim 4 further comprising means for switching various ones of said fluorescent lamps on and off to control the intensity of the light output.

6. The combined work station and phototherapy unit of claim 4 wherein said fluorescent lamps produce a full spectrum energy output including ultraviolet energy.

7. The combined work station and phototherapy unit of claim 4 wherein said fluorescent lamps produce a daylight spectrum energy output without ultraviolet energy.

8. The combined work station and phototherapy unit of claim 4 wherein said fluorescent lamps produce a distribution of narrow spectral bands which increases lumen output and approximately doubles illuminance at the eye.

9. The combined work station and phototherapy unit of claim 4, further comprising means for detachably mounting said light fixture to said vertically extending walls of said base unit.

10. The combined work station and phototherapy unit of claim 4 further comprising means for attaching said light fixture to said vertically extending walls of said base unit, said attaching means permitting said fixture to be rotated relative to said work station.

11. The combined work station and phototherapy unit of claim 1 wherein said fixture is mounted at an angle in the range of between about 40° and 45° relative to the horizontal.

12. The combined work station and phototherapy unit of claim 11 further comprising means for detachably mounting the fixture to the base unit including at least one extending arm on one of the light fixture and base unit and mating arm receiving means on the other.

13. The combined work station and phototherapy unit of claim 11 and further comprising diffuser means on said fixture means.

14. The combined work station and phototherapy unit of claim 1 wherein the light fixture supplies visible light at an intensity in the range from about 2,500 to about 10,000 lumens with the person positioned at a normal working distance relative to the work space of the work station.

15. The combined work station and phototherapy unit of claim 14 wherein the light fixtures supplies about 10,000 lumens of visible light to the user position at a normal distance relative to the work station.

16. The combined work station and phototherapy unit of claim 4 wherein the fluorescent lamps of said bank of lamps are elongated and extend the length of the fixture.

17. The combined work station and phototherapy unit of claim 1 wherein said means for mounting said light fixture to said base unit comprises removable mounting means and means for assembling said lamp fixture to said base unit to be moved as a combined unit.

18. The combined work station and phototherapy unit of claim 1 wherein a portion of the visible light produced by the electric lamp is directed to the work space for its illumination.

* * * * *